(12) United States Patent
Kauling et al.

(10) Patent No.: US 9,809,792 B2
(45) Date of Patent: *Nov. 7, 2017

(54) ONE-WAY SEPARATOR FOR RETAINING AND RECIRCULATING CELLS

(71) Applicant: BAYER AKTIENGESELLSCHAFT, Leverkusen (DE)

(72) Inventors: Joerg Kauling, Bergisch Gladbach (DE); Juri Seletzky, Berkeley, CA (US); Jorgen Magnus, Dusseldorf (DE); Andre Pastor, Solingen (DE); Helmut Brod, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 474 days.

This patent is subject to a terminal disclaimer.

(21) Appl. No.: 14/379,577

(22) PCT Filed: Feb. 20, 2013

(86) PCT No.: PCT/EP2013/053390
§ 371 (c)(1),
(2) Date: Aug. 19, 2014

(87) PCT Pub. No.: WO2013/124326
PCT Pub. Date: Aug. 29, 2013

(65) Prior Publication Data
US 2015/0017716 A1    Jan. 15, 2015

(30) Foreign Application Priority Data
Feb. 20, 2012  (EP) .................................. 12001121

(51) Int. Cl.
*C12M 1/12* (2006.01)
*C12M 1/26* (2006.01)
(Continued)

(52) U.S. Cl.
CPC ............ *C12M 33/22* (2013.01); *C12M 23/06* (2013.01); *C12M 23/14* (2013.01); *C12M 23/26* (2013.01);
(Continued)

(58) Field of Classification Search
CPC ...... C12M 23/06; C12M 23/14; C12M 23/26; C12M 23/28; C12M 27/16; C12M 29/04; C12M 33/22
See application file for complete search history.

(56) References Cited

U.S. PATENT DOCUMENTS 4,268,392 A * 5/1981 Hayes ..................... E03C 1/264
210/238
4,783,255 A * 11/1988 Bogusch ............ B01D 21/0051
210/522
(Continued)

FOREIGN PATENT DOCUMENTS

AU      4118497 A     3/1998
CA      2458980 A1    3/2003
(Continued)

OTHER PUBLICATIONS

English language machine translation of DE 10223536 (Dec. 18, 2003), pp. 1-8.*
(Continued)

*Primary Examiner* — William H Beisner
(74) *Attorney, Agent, or Firm* — McBee Moore Woodward & Vanik IP, LLC

(57) ABSTRACT

The invention relates to a separator for retaining and recirculating cells in a continuous-flow or batch-flow type plastic bag or bottle, which can preferably be operated outside of a bioreactor. Additionally, the invention relates to a method for retaining and recirculating cells within or outside a (Continued)

Figure 1:
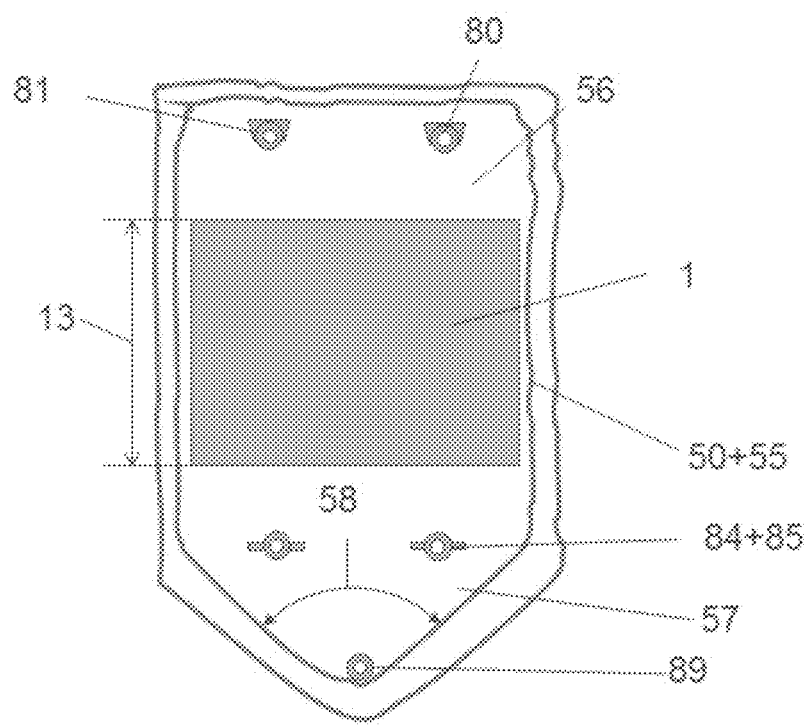

bioreactor. The invention further relates to a method for producing the separator according to the invention.

15 Claims, 14 Drawing Sheets

(51) Int. Cl.
*C12M 1/00* (2006.01)
*C12M 3/06* (2006.01)

(52) U.S. Cl.
CPC ............ *C12M 23/28* (2013.01); *C12M 27/16* (2013.01); *C12M 29/04* (2013.01); *C12M 47/02* (2013.01)

(56) References Cited

U.S. PATENT DOCUMENTS

| | | |
|---|---|---|
| 4,814,278 A | 3/1989 | Hamamoto et al. |
| 5,225,346 A | 7/1993 | Matsumiya et al. |
| 5,320,963 A | 6/1994 | Knaack et al. |
| 5,350,527 A | 9/1994 | Kitko |
| 5,698,102 A | 12/1997 | Khudenko |
| 5,817,505 A | 10/1998 | Thompson et al. |
| 6,186,932 B1 | 2/2001 | Vallot |
| 6,959,618 B1 | 11/2005 | Larsen |
| 2009/0180933 A1 | 7/2009 | Kauling et al. |
| 2011/0070648 A1 | 3/2011 | Anneren et al. |
| 2011/0097800 A1 | 4/2011 | Kauling et al. |

FOREIGN PATENT DOCUMENTS

| | | |
|---|---|---|
| DE | 7215337 U | 8/1972 |
| DE | 2548950 A1 | 5/1977 |
| DE | 4401576 A1 | 7/1995 |
| DE | 10223536 A1 | 12/2003 |
| DE | 102010015236 A1 | 10/2011 |
| EP | 0471947 A1 | 2/1992 |
| EP | 0599651 A2 | 6/1994 |
| EP | 0699101 A1 | 3/1996 |
| GB | 2339763 A | 2/2000 |
| NZ | 335559 A | 4/2000 |
| WO | WO-94/26384 A1 | 11/1994 |
| WO | WO-9807828 A1 | 2/1998 |
| WO | WO-9958222 A1 | 11/1999 |
| WO | WO-0005337 A1 | 2/2000 |
| WO | WO-03020919 A2 | 3/2003 |
| WO | WO-2009139703 A1 | 11/2009 |
| WO | WO-2009152990 A2 | 12/2009 |
| WO | WO-2011142670 A1 | 11/2011 |

OTHER PUBLICATIONS

International Search Report, PCT/EP2013/053390.
Henzler, H.-J., Chemie-Technik, 1, 1992, 3.
Binder, H.-J., Sedimentation aus Ein- und Mehrkornsuspensionen in schräg stehenden, laminar durchströmten Kreis- 5 und Rechteckrohren [Sedimentation from single- and multi-grain suspensions in inclined, laminar-flow circular and rectangular tubes], Dissertation Berlin, 1980 (Translation).

* cited by examiner

ONE-WAY SEPARATOR FOR RETAINING AND RECIRCULATING CELLS

CROSS REFERENCE TO RELATED APPLICATIONS

This application is a national stage application (under 35 U.S.C. §371) of PCT/EP2013/053390, filed Feb. 20, 2013, which claims benefit of European application no. 12001121.8, filed Feb. 20, 2012, the entire contents of all are hereby incorporated by reference.

The invention relates to a single-use separator for retaining and recirculating cells in a continuous-flow or batch-flow type plastic bag, which preferably can be operated outside a bioreactor. The invention further relates to a method for retaining and recirculating cells within or outside the bioreactor according to the invention. In addition, the invention relates to a method for producing the separator according to the invention.

Animal and plant cell culture is of great importance in the production of biologically active substances and pharmaceutically active products. In particular, cell culture, which is frequently carried out in a nutrient medium in free suspension, is demanding, because the cells, in contrast to microorganisms, are very sensitive with respect to mechanical shear stress and insufficient supply with nutrients.

Usually, animal and plant cell lines are cultured batchwise. This has the disadvantage that an optimum supply of the cells may be achieved only with difficulty because of the constantly changing concentrations of substrate, product and biomass. At the end of the fermentation, furthermore, byproducts accumulate, e.g. components of dead cells, which usually must be removed with great expenditure in the later workup. For the stated reasons, but in particular in the case of the production of unstable products which can be damaged, e.g., by proteolytic attacks, continuously operated bioreactors are therefore used.

Using continuous bioreactors, high cell densities and an associated high productivity may be achieved if the following requirements are met:
  an adequate and low-shear supply of the cells with substrates, in particular dissolved oxygen,
  an adequate disposal of the carbon dioxide formed in respiration,
  an effective, low-shear, non-cloggable cell retention system for building up high cell concentrations,
  long-term stability (sterility, hydrodynamics) of the bioreactor and retention system.

In addition to the continuous procedure, a bioreactor having an efficient cell retention system can also be used, e.g., for culturing starter cultures having particularly high cell densities. The cell retention system is then used in a discontinuous manner in the repeated-batch mode, in order to withdraw cell culture supernatant virtually free of biomass. Thereafter, the starter culture reactor can again be charged with fresh nutrient medium in order to bring the culture in this manner to higher cell densities than in a simple batchwise mode.

In order that a high cell density (>20 million live cells per milliliter) can be achieved in a continuously operated bioreactor, efficient retention of the cells is necessary. The required degree of retention depends in this case on the growth rate of the cells and on the perfusion rate q/V (media throughput q per bioreactor volume V).

In the past, differing cell retention systems have been proposed for continuously operated bioreactors which are usually arranged outside the bioreactor. The reason for this is the easy accessibility of the cell retention system for maintenance and cleaning purposes.

In order to keep as low as possible cell damage, in particular owing to inadequate oxygen supply and carbon dioxide removal outside the bioreactor, and also degradation of active ingredients owing to enzymatic attacks, cell retention systems having small working volumes and associated short residence times of the cells are desirable.

In addition to membrane filters, apparatuses which operate according to the principle of cross-flow filtration with stationary and moving membranes, in the prior art special centrifuges and gravity separators are used.

In the case of cell retention using membrane filters, deposits or soilings are observed, which can prevent reliable and maintenance-free long-term operation. The deposits can be reduced if the flow over the membrane surfaces is sufficiently fast. This can be achieved in steady-state or oscillating operation. One example of oscillating flow over a membrane system is the alternating tangential flow (ATF) system from Refine Technologies Inc. The rapid flow over the membrane surfaces, however, runs counter to the basic condition of low-shear cell culture.

Low-shear centrifuges for separating off cells in the centrifugal field operate for only a few weeks without maintenance expenditure and require replacement of the centrifuge elements. The risk of contaminations is increased thereby.

The gravity separators predominantly used in cell culture are settling tanks and inclined channel separators. Compared with simple settling tanks, the inclined channel separators on large scales have the advantage of considerably lower volume in relation to the separation area. A publication (Henzler, H.-J., Chemie-Technik, 1, 1992, 3) describes cell retention in inclined channel separators which can be operated in counterflow, crossflow and in co-current flow. The flow-bearing channel cross section can be provided with plates or tubes. The patent documents U.S. Pat. No. 5,817,505 and EP 0 699 101 B1 claim the use of inclined channel separators for retaining cells in counterflow separators. In WO2003020919 A2, inter alia, counterflow and crossflow separators are described for the retention of cells, and also combinations with various preliminary separators (e.g. hydrocyclones).

The inclined channel separators are attached to the bioreactor via an external circuit. For this purpose, flexible tubes and pumps are required.

In order to decrease the metabolic activity and the clumping of cells in a gravity separator, cooling down the cell culture broth on its path to the gravity separator is proposed. A reduced metabolic activity at low temperature is certainly advantageous in the case of a relatively long residence of the cells outside the bioreactor.

WO2009152990(A2) describes a cell retention system for retaining and recirculating cells in a flow-bearing vessel, comprising a multiplicity of adjacently arranged channels, wherein the channels form an upright hollow cylinder and are inclined at an angle β between 10° and 60° to the longitudinal axis of the hollow cylinder. The flow-bearing vessel can be a bioreactor or a vessel for cell retention and recirculation which is connected to a bioreactor. The channels are open at the lower end. At the top end, they lead into a shared annular space which has at least one conduit via which a harvest stream can be transported from the vessel. In the channels, cells and cell culture solution are separated. Owing to the continuous removal of the harvest stream from the bioreactor, cell culture solution and cells are drawn by suction into the channels. The cells sediment within the channels that are arranged at an incline and slide, as in classical inclined channel separators, in counterflow to the influent harvest stream back out of the channels and therefore remain in the vessel. The cell culture solution that is separated from the cells is transported through the channels into the annular space above the channels and finally out of the vessel.

In the case of highly regulated pharmaceutical production, a large expenditure in terms of time, apparatus and personnel is allocated to the provision of purified and sterilized bioreactors and bioreactor elements such as, for example, cell retention systems. In order to avoid reliably crosscontaminations during product change in a multipurpose plant or between two product batches, apart from the cleaning, a very complex cleaning validation is required, which may need to be repeated in the case of a process adaptation. For cleaning and sterilization of conventional batch, fed-batch or perfusion fermenters made of stainless steel, generally the clean-in-place (CIP) technique is used in combination with the steam-in-place (SIP) technique in what are termed permanently piped systems. In order to ensure sufficient long-term sterility in a continuous process procedure, the autoclaving technique is also used which, however, requires laborious transport of the reactors or reactor elements to the autoclave and is only applicable in comparatively small reactor scales. The risk of contamination is particularly critical when aging wearing parts are used, e.g. sealed stirrer shafts, in the case of incorrect sterilization or plant transport, start-up or the attachment of connection conduits after autoclaving and regular sampling.

In the case of CIP/SIP systems used in the batch mode or fed-batch mode, the loss of use of a reactor due to the provision procedures, in particular in the case of frequent product change, in view of the short periods of use, can be in the magnitude of the reactor availability.

In order to accommodate the requirement for rapid and flexible new charging of the production system, with maintenance of maximum cleanliness and sterility, designs for single-use reactors are enjoying constantly increasing interest on the market.

Therefore, proceeding from the prior art, the object is to provide an efficient method for retaining and recirculating animal, in particular human, and plant cells in a continuous or batchwise method, which takes into account the sensitivity of the cells with respect to mechanical shear stress and adequate supply of the cells with nutrients, is scalable up to very large scales, which meets the maintenance, cleaning and sterilizing requirements of the pharmaceutical industry, the use of which decreases complexity and the risk of error, and which, with minimal use of resources, permits an economically and ecologically optimal utilization (production and disposal) as single-use systems.

The abovementioned object was achieved by a single-use cell separator for retaining and recirculating cells from a bioreactor mixture, comprising a flow-bearing plastic bag which is sterilizable by the prior art, e.g. preferably gamma-irradiatable, autoclavable or chemically sterilizable, or a correspondingly treatable plastic bottle having the following internals:

in the upper region of the plastic bottle or of the plastic bottle, one or more passages/internals (80) for withdrawing a harvest stream (70) (=harvest) from a harvest stream collection region 56, which harvest stream is separated from the cells in the upper segment of a central region of the plastic bag, a separation region comprising a separation area (500) or a lamellae pack (1) containing the separation area, which lamellae pack, during operation, is inclined to the horizontal at an angle (10=β) of 0° to 80°, in the lower segment of the central region of the plastic bag or of the plastic bottle, one or more passages or internals (84), optionally having a horizontal distributor (85), for the uniform horizontal flow distribution of the cell culture solution (=feed) (74) over an introduction surface (510), in the lower region of the plastic bag or of the plastic bottle, a solids collection region (57) that is tapered conically at the bottom for collecting the cells with the aid of gravity. Usually, the solids collection region (57) has one or more passages (89) or internals (88) for withdrawing the cells.

The invention therefore relates to a solids separator for retaining solids from a reactor mixture, comprising a flow-bearing sterilizable plastic bag or plastic bottle and, within the plastic bag or plastic bottle:

in the upper region, one or more passages/internals (80) for withdrawing from a harvest stream collection region (56) a harvest stream (70) that is separated from the solids, in the upper segment of a central region, a separation region (1, 501) having a separation area which during operation is inclined at an angle (10=β) of 0° to 80° to the horizontal, in the lower segment of the central region, one or more passages or internals (84), optionally having a horizontal distributor (85), for the uniform horizontal flow distribution of the reactor mixture (74), in the lower region a downwardly, usually conically or pyramidally, tapered solids collection region (57) for collecting the solids using gravity.

Usually, the solids collection region (57) has one or more passage (89) or internals (88) for withdrawing the solids. The solids can thereby be recirculated into the reactor as required.

Preferably, the downwardly tapered solids collection region has an angle 58, 59 of 10° to 60° to the vertical, wherein the angles 58 and 59 are individually selectable.

The shape of the harvest stream collection region 56 can be as desired, in particular flat or upwardly tapered.

Usually, the plastic bag or the plastic bottle is constructed of a single- or multilayer transparent polymer material which permits a view into the device during operation.

The polymer material of the plastic bag, at usual low film thicknesses of s<1 mm, permits apparatuses having a comparatively small mass fraction. It is inexpensive to provide and to process, which is very highly suitable for construction of single-use systems. The disposal of used separators and the use of a new single-use separator are therefore more economical than cleaning used separation devices, in particular since, in the case of use of single-use separators, expensive cleaning with water for injections (WFI) and the time-consuming cleaning validation is dispensed with. The separator according to the invention is preferably assembled suitably for connection to the bioreactor system via flexible tubes having corresponding sterile-couplable connection elements and filter elements, and sterile-packed.

As materials for the plastic bag, in particular the materials and material combinations used in the U.S. Pat. No. 6,186,932 B1 in columns 2 and 3 for the transport bags (sachets) cited there are suitable. Also, the wall thicknesses listed there may be applied to the separation device according to the invention.

In a preferred embodiment, the walls of the plastic bag consist of a film composite material known to those skilled in the art made of two or more layers (laminate or co-extrudate), in order to improve the properties of the plastic bag with respect to unfolding behavior, expansion behavior, gas diffusion, stability, process compatibility (minimal adsorption of products and cells) and weldability.

The solids separator according to the invention with a plastic bag made of polymer films can be produced, for example, by the method described in U.S. Pat. No. 6,186,932 B1, wherein the weld seams need to be adapted. Exemplary embodiments for producing preferred embodiments of the separation device according to the invention are described further hereinafter.

Passages are usually produced from the same material of which the product-contact film also consists, in order to permit sterile and strength-related fault-free welding thereby. A preferred product-contact film material is polyethylene of various degrees of crosslinking known to those skilled in the art. As outer shell films, depending on application and process requirement, various materials known to those skilled in the art having a melting point increased compared with the inner film for use of thermal welding methods and/or improved strength and/or diffusion properties are used.

Usually, the internals 80, 88 and 84 are welded-in passages, to which conduits, preferably flexible tubes for connection to the bioreactor or other external systems, can be connected. Alternatively, the passages, for the passage through of the connection lines, can be introduced into one or more connection plate(s), covers or stoppers.

In a particular embodiment of the separator according to the invention, in the upper region, on the wall of the plastic bag (tetrahedron) or at a corner (cube), one or more connection plates 90 are situated, preferably one, which can also be a cover, which contains the passages for passing through the connection lines and, in the region of the connection, a support of the separator is made possible. It is usually connected to the housing of the separator during assembly.

Alternatively, at the end of the tapered solids collection region 57, at a neck, a cover or a stopper 220 can be introduced. Cover or stopper comprise in this embodiment the passages for passing through the connection lines.

The solids are usually taken off from the solids collection region 57 via one or more passages or internals 88 in the vicinity of the lower apex of the separator. The internal 88 is usually connected to the bioreactor into which the collected cells are recirculated via the pressure gradient or via pumps. Preferably, the internal 88 is used for central vertical removal of the solids by suction. This simplifies the production and placing of the separator in the container thereof for operation. Also, the takeoff can also proceed via a passage welded into the apex of the separator or via a passage introduced in a cover or stopper.

In a first embodiment of the present invention, the separation region consists of a multiplicity of adjacently arranged channels in a lamellae pack 1, preferably produced from a plurality of ridgeplates stacked one above the other which form the channels of the lamellae pack 1. Preferably, plastic plates are used. The channels are open at the bottom end and at the upper end. At the bottom end, the channels lead to the introduction surface via the shared downwardly, in particular conically or pyramidally, tapered solids collection region 57. At the upper end, they lead to a shared harvest stream collection region 56 which has at least one passage 80 through which the harvest stream can be transported out of the vessel.

In the channels, cells and cell culture solution are separated. Via the continuous removal of the harvest stream from the bioreactor, cell culture solution and cells are drawn into the channels by suction. In the lower segment of the central region of the plastic bag or of the plastic bottle, one or more passages or internals 84 are introduced for uniform horizontal flow distribution of the reactor mixture 74. A uniform horizontal flow distribution of the cell culture solution (=feed) 74 is sought via an introduction surface 510. Usually, depending on the width of the lamellae pack, one to four passages having straight ports are introduced at the same height in the wall plastic bag or of the plastic bottle. Depending on the height and distance between such passages, horizontal distributors 85 can be advantageous as internals.

The cells sediment within the channels that are arranged at an incline, slide, as in classical inclined channel separators, in counterflow to the influent harvest stream back out of the channels and collect in the conically tapered solids collection region 57. Usually, the solids collection region 57 has one or more passages/internals 88/89, connected to the bioreactor for removing the collected cells by suction and recirculation into the bioreactor.

Figure 4:
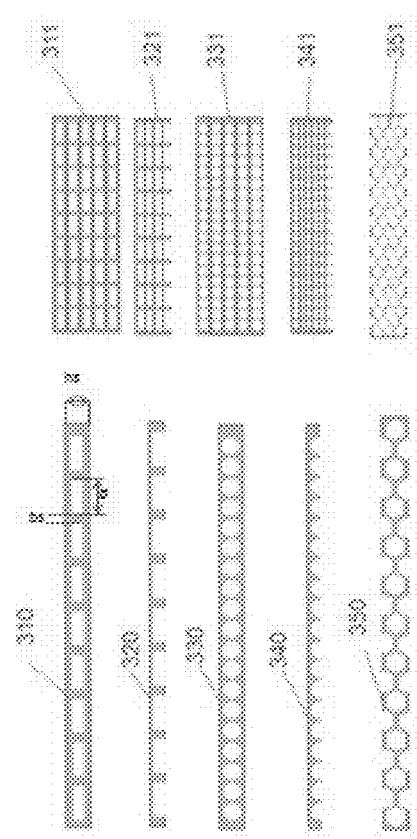

The channels of the lamellae pack 1 can have a rectangular, elliptical, round or semiround cross section (FIG. 4).

The dimensioning of the channels (number, diameter, length) depends in each case on the type of cells that are to be retained, on the size of the bioreactor and on the throughput.

The channel width d is preferably d≥1 mm, in order to prevent blockage of the channels. In a preferred embodiment, channels having a channel width of 3 mm to 100 mm are used, preferably 4 mm to 20 mm, particularly preferably 5-7 mm, in order firstly to prevent blockage states safely, but secondly to keep as low as possible the volume ratio of separator and bioreactor space that decreases the space-time yield.

The required separation area $A_{erf}$ results from the sedimentation velocity ws, the perfusion rate q/V (media throughput q per unit bioreactor volume V) and the bioreactor volume according to Eq.1.

An efficiency coefficient η takes into account the reduction in performance or difference in performance of inclined channel separators in comparison with vertical separators (Eq.2).

The theoretical separation area $A_{th}$ for rectangular and cylindrical cross sections can, according to approaches published in the literature (H.-J. Binder, Sedimentation aus Ein- und Mehrkornsuspensionen in schräg stehenden, laminar durchströmten Kreis- und Rechteckrohren [Sedimentation from single- and multi-grain suspensions in inclined, laminar-flow circular and rectangular tubes], Dissertation Berlin, 1980), be determined to an approximation from Eqs. 3 and 4:

$$A_{erf} = \frac{\text{Perfusion rate} \cdot V}{ws} \quad \text{(Eq. 1)}$$

$$A_{th} = \frac{A_{erf}}{\eta} \quad \text{(Eq. 2)}$$

$$\text{Rectangle: } A_{th} \approx Z \cdot \sin(\beta) \cdot d \cdot L \quad \text{(Eq. 3)}$$

$$\text{Cylinder: } A_{th} \approx \frac{3 \cdot \pi}{16} \cdot Z \cdot \sin(\beta) \cdot d \cdot L \quad \text{(Eq. 4)}$$

Here, Z is the number of the channels, β is the angle by which the channels are tilted with respect to the direction of gravity, d is the internal diameter and L is the length of the channels. π is pi (π=3.14159 . . . ).

When the channel length is being dimensioned, maintaining laminar flow conditions (Reynolds number Re<2300) must be taken into account. The channel length L is oriented according to the length of the available bag inner dimension (=length of the bag LK). The bag length LK to be implemented is oriented according to the fill levels to be achieved in the plastic bag and on the hydrostatic pressures to be achieved in the plastic bag. Excessive hydrostatic pressures may possibly be passed on to appropriately dimensioned, non-product-contact and therefore reusable housings.

The dynamic pressure at the harvest stream takeoff site (=passages/internals 80) should in this case be at least 5- to 10-times lower than the pressure drop in the channels, in order to exclude the maldistribution phenomenon that decreases efficiency. Adequate pressure drops are considered technically realizable for channel lengths from 0.1 m, whereas preferably channel lengths of 0.2 m to 5 m, particularly preferably channel lengths of 0.4 m to 2 m, are implemented.

Usually, the channel lengths L is 30% to 95%, particularly preferably 60% to 90%, of the length LK of the plastic bag or of the plastic bottle.

Short channel lengths L, on account of the reduced pressure drops, can lead to distribution problems, which, in particular, when the harvest stream is removed from the upper harvest stream collection region 56, can require a distribution device for reducing the takeoff velocities. Optionally, therefore, the passages/internals 80 have flow inverters 81 for a uniform takeoff of the harvest stream 70 (=harvest) separated from the cells from a harvest stream collection region 56.

The separator according to the invention can usually comprise 1 to $10^6$ channels, preferably 10 to 100 000, particularly preferably 10 to 10 000. The channels may be distributed over one or more ridgeplates in a lamellae pack 1 for optimizing the space requirement. Preferably, the lamellae pack 1 comprises from 1 to 400 ridgeplates, particularly preferably 1 to 50 ridgeplates. In an embodiment which does not restrict the invention, the ridgeplates can be joined to a support plate 30, which offers support and can be joined to the plastic bag by adhesion or welding for exact positioning.

The width to height ratio of the lamellae pack 1 consisting of single- or multilayer ridgeplates including the support plate may be adapted to the geometry of the plastic bag.

In 3D bags (bags made from 4 film webs welded together), expediently lamellae packs 1 having a square, cylindrical rectangular or elliptical cross section having a height to width ratio H/D of 0.3<H/D<1.5, preferably 0.6<H/D<1.2, particularly preferably 0.9<H/D<1.0 may be used.

For the simpler, more inexpensive 2D bags (bags made from two film webs welded together), flat lamellae packs having a rectangular cross section with H/D ratios of 0.005<H/D<1, preferably 0.02<H/D<0.6, particularly preferably 0.04 are suitable.

For welding together a 2D bag with an inserted lamellae pack, it is advantageous to keep a minimum spacing ratio $0.5 \leq X/H \leq 2$, preferably $1 \leq X/H \leq 1.6$, wherein X is the distance between the lamellae pack 1 and the start of a tapering and H is the thickness of the lamellae pack. The lamellae pack 1 can be formed from a profiled plate 340 or 320 (see FIG. 4). A profiled plate preferably has a smooth side and a side having a sequence of ridges and channels at constant distances. Channels form on stacking the plate in one or more layers e.g. on a support plate 30. In this case, the channels are closed towards the open side in each case by the smooth side of an adjacent layer or by the wall of the stator. Likewise there is the possibility of extruding a lamellae pack or partial pack in a single or multilayer manner, and joining it to form a lamellae pack 1.

The geometry of the channels is established by the ratio of the ridge height hs to the channel width d (FIG. 4). Technically achievable hs/d ratios, depending on properties (shapeability, elasticity, deep-drawing capacity) are in the range $0.01 \leq hs/d \leq 5$. Usually, hs is greater than or equal to 1 mm, or preferably should be greater than or equal to 3 mm. Preferred hs/d ratios are 0.5 to 5. The ridge widths bs are determined by the mechanical stability of the film material. The ridge widths bs should be as small as possible in order to enable high separation areas per unit of separator volume. At the same time, they should not be selected to be excessively small, in order to permit a frictional connection to the lower layer without shape change. In the case of extruded lamellae packs 1, or in the case of lamellae packs which are made up from extruded lamellae part packs or ridgeplates, very high stiffnesses with small ridge widths can be achieved without great loss of separation area, and so this production form is preferred.

The lamellae pack which is made up of ridgeplates is either designed as a rectangular parallelepiped (FIG. 3), wherein the plane of the channel openings is at a right angle to the contact surface of the lamellae pack 1, or as an oblique parallelepiped (FIG. 2), wherein the channel openings in the built-in state lie on a horizontal plane. The latter solution is preferred in order to prevent a concentration gradient caused by sedimentation towards the lower channel openings. The channels preferably receive reactor mixture flow evened out with the aid of the horizontal distributor (85).

A preferred connection of the ridgeplates is made via adhesion or welding. The lamellae pack should primarily be fixed in space by the connection. In addition, attempts are made to keep as small as possible what are termed the dead zones (spaces which are not used for separation and are around the external surfaces of the ridgeplates). However, a complete avoidance of these dead zones is not necessarily required here. Suitable adhesives are the adhesive components which are known to those skilled in the art and are matched to the material and surface properties of the channels. In particular, an adhesive is preferably used which is available on the market in the required FDA quality classes. For welding, thermal joining techniques such as heat, laser, ultrasound may be used. A particularly preferred joining technique is laser beam welding which can be employed, in particular, also in combination with the cutting of the lamellae pack in a device suitable therefor. The welding technique has the advantage that the number of plastics introduced into the pharmaceutical process is not increased by this joining technique.

The profiled plate can result by shaping directly during plate production or via (e.g. adhesion) joining of an embossed, hot- or cold-formed plate to a smooth plate. The material properties of the embossed and smooth plates can be optimally adapted, e.g. by selecting a suitable material known to those skilled in the art and having appropriate surface quality, to the differing functionality thereof (good sliding properties and shape stability of the embossed plates, good density properties of the smooth plates).

Usually, commercially available, inexpensive ridgeplates that are suitable for pharmaceutical processes, in particular plastic ridgeplates, are extruded, e.g., from polycarbonate, and, as lamellae partial packs, for producing lamellae pack 1, cut or produced and fastened together in the appropriate length.

For producing the separator, in addition, in a plastic film, the passages and further internals are prepared and optionally installed at the proper sites.

Then a plastic bag 50 is welded together (FIG. 5) from the plastic film which encloses the lamellae pack 1 in a plastic bag 50 having a weld seam 55.

The lamellae pack 1 including the support plate is then usually pressed against the inner surfaces of the plastic bag 50 in order to prevent the penetration of cells between plastic bag 50 and lamellae pack 1 and thus prevent fouling.

In a first embodiment of the production method, the plastic bag 50 is stretched onto the lamellae pack 1 (FIG. 5) and the fold 52 which is formed is pressed flat and fastened (FIG. 6) by means of one or more fastening strips 60. A suitable fastening strip is also a plastic film which is wound tightly round bag and lamellae pack. Favorable stretching properties are possessed by, e.g., domestic films or flexible thin films made of silicone. Also, welding of the lamellae pack 1 to the bag wall can be suitable for producing a tight connection between bag and lamellae pack.

The methods described permit simple and inexpensive production of the solids separator according to the invention for retaining and recirculating cells. Via the configuration of the lamellae packs which is variable in broad limits, the geometry of the later device may be established simply and accurately, and, in contrast to systems made of stainless steel, also provide for very large bioreactors. The methods described in particular permit the inexpensive production of single-use elements, the use of which can reduce to a minimum the expenditure for provision of a retention system purified according to the pharmaceutical principles.

For operation, the device according to the invention is orientated at an angle $10=\beta$ to the horizontal. The angle $\beta$ depends on the settling and sliding behavior of the cells/solids and, during operation, is $30°\leq\beta\leq80°$ to the horizontal. In a preferred embodiment, the angle $\beta$ is 35° to 75°, particularly preferably 45° to 60° to the horizontal.

Figure 11:
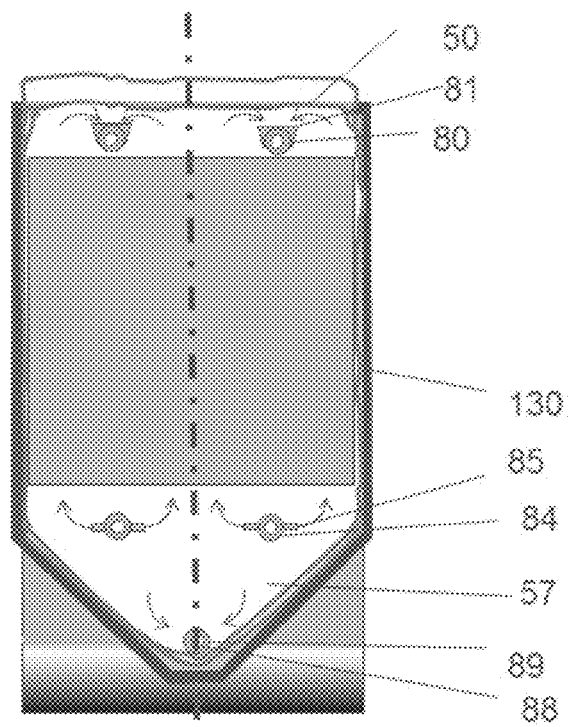
Figure 12:
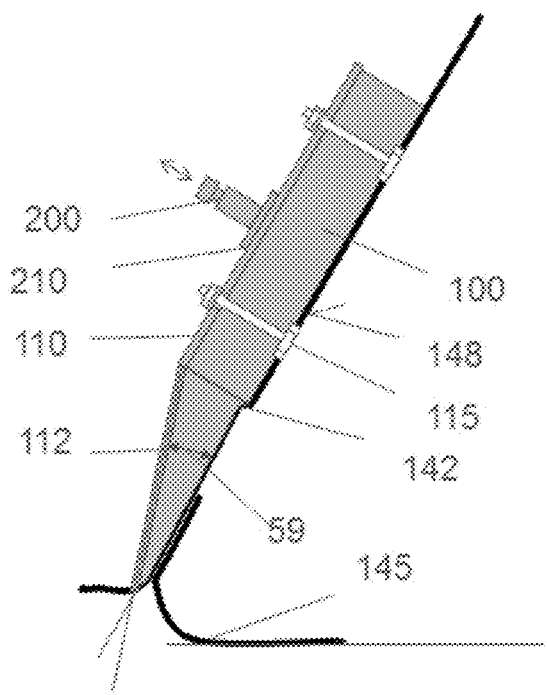
Figure 13:
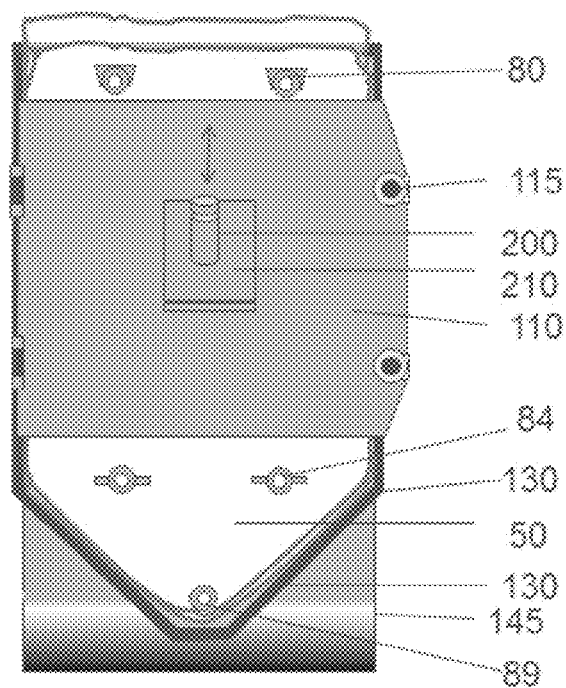

In order to ensure the angle $\beta$ during operation, the solids separator according to the invention, for operation, is fastened to a stand 140 (FIGS. 11 to 13).

Usually, the stand 140 comprises a stand foot 145 and a support 148 having a predefined angle 10 ($=\beta$) to the set-up area. On the support 148, the lamellae pack 1 including the support plate 30 is fixed at a predefined height using a projection 142 and/or cover 110, and also fastening elements 115, in order that both the harvest stream collection region 56 (top) and the solids collection region 57 can rest on the support as far as possible without folds during operation. Dead spaces and corresponding fouling are thereby reduced.

In a preferred embodiment, the stand 140 has a housing 100 and a cover 110 for receiving the lamellae pack 1.

In this case, the stretching process can also take place during incorporation of the solids separator according to the invention onto the stand 140, and in particular in the housing 100 and cover 110 (FIGS. 6 and 7) optionally also without coiling using a fastening strip 60. In this case, the plastic bag 50 is held in position onto the support plate 30 and onto the lamellae pack 1 with the aid of the housing 100, and the fold 52 is pressed onto the lamellae pack 1 with the aid of the cover 110. Preferably, the cover 110 is fixed on the housing 130 on one side, e.g. by means of hinges, and on the other side by means of one or more closable fastening elements 115. The stand 140 is thereby simpler to actuate for starting up the solids separator according to the invention.

In a preferred embodiment, the cover 110 has an elongation 112 and/or a frame 130 which keeps the downwardly tapered solids collection region 57 in shape, in particular the angle 59 constant, and prevent the extending thereof in the filled state during operation. Such a shape-fitting container is advantageous, inter alia, for operating the system under relatively large hydrostatic loads, as may be expected on attachment to large bioreactors.

To improve the sliding behavior of the cells in the channels of the lamellae pack and on the inner walls of the downwardly, in particular conically or pyramidally, tapered solids collection region, the device can be made to vibrate using suitable means, for example pneumatic or electric vibrators.

The separation areas required are oriented according to the sedimentation properties of the cells and also the sought-after perfusion rates and cell concentrations. Preferred perfusion rates are in the range from 0.1 to 40 l/day, particularly preferably from 0.5 to 20 l/day. Preferred separation areas per unit bioreactor volume, depending on sedimentation properties of the cells (dependent on the concentration, size and agglomeration tendency of the cells), are in the range from 0.1 to 100 $m^2/m^3$, particularly preferably 2 to 20 $m^2/m^3$.

Alternatively to the plastic bag, a lamellae pack 1 can be installed in a plastic bottle 50 having a polygonal cross section (FIG. 21), wherein the plastic bottle has a downwardly tapered region which ends in a bottleneck and wherein the downwardly tapered region forms the solids collection region 57 for collecting the solids with the aid of gravity. For operation, the plastic bottleneck is closed using a cover 220, which has the passages for passing through the connection lines. In an alternative embodiment, the lamellae pack 1 is replaced as separation region by one or more bases fastened to the walls of the plastic bottle 50.

A suitable material for the plastic bottle is, e.g., the material from the commercially available Millicell® culture bottles from Merck Millipore from (http://www.millipore.com/catalogue/module/c85149).

The solids separator according to the invention is preferably designed as a single-use article to avoid the cleaning problems.

Figure 18:
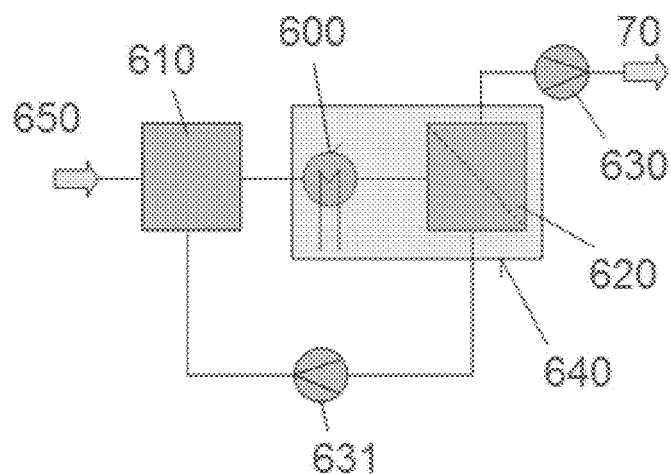

Usually, the cell separator according to the invention is externally coupled by means of flexible tubes to a bioreactor, e.g. to a single-use bioreactor as described in US 2009-0180933. Supply of the separator according to the invention is ensured via at least two pumps, preferably low-shear peristaltic pumps (FIG. 18). The pumps permit the withdrawal of the cell culture solution from the bioreactor space, the feed thereof, after cooling via a heat exchanger, to the separation device, the removal of the harvest stream from the separation device, and the return transport of the solids stream ($=$return 70) to the bioreactor.

Storage of the solids separators according to the invention is space-saving, since they can be stacked one above the other without problem and are only set to the suitable angle on starting operation. They may then be simply connected outside a bioreactor and operated. They are connected to the fermenters by means of sterile couplers from various manufacturers (Pall, Sartorius, Coulder) which are fastened at the end of the flexible tubes, inside or outside safety working benches, but preferably by flexible tubular welding. The flexible tubes fastened on the solids separators according to the invention are therefore preferably—at least in part—equipped with a flexible tube element suitable for flexible tubular welding. In addition, the flexible tubes, for transporting the suspension usually contain at least two special tubular elements able to bear high mechanical load (e.g. made of elastomeric flexible tube Verderprene from Verder), which can be laid noninvasively into peristaltic pumps, without endangering the sterility of the separators. The connection, the operation and maintenance are problem-free. The design of the device according to the invention or parts of the device according to the invention as single-use element eliminates cleaning problems.

Further items of the present invention are therefore a method for preparing a solids separation device according to the invention having a lamellae pack in a plastic bag and A direct insertion of the lamellae pack 1 into aerobic bioreactors is conceivable in principle when the gas bubbles required for gassing can be kept remote from the intake openings. In this case, the conical collection part of the plastic bag can be dispensed with, as can the reflux pump. Preferably, the separator according to the invention, however, is provided for use outside a bioreactor.

In a second embodiment of the cell separator according to the invention, the plastic bag is polyhedral or conical, wherein the plastic bag, during operation, is placed such that the solids collection region 57 which is tapered conically at the bottom is formed by the walls of the plastic bag and an apex or corner of the polyhedron or of the cone. Within the plastic bag, the angle 10 of the separation area 500 is at 0° to the horizontal, as in conventional vertical separators.

The volume of the separator can have values, for example, of 0.1 l to 1000 l.

Figure 14:
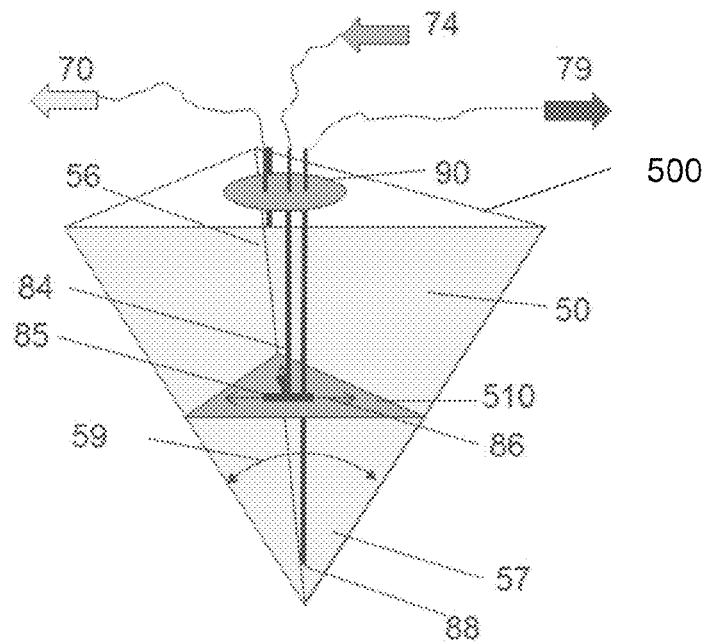
Figure 15:
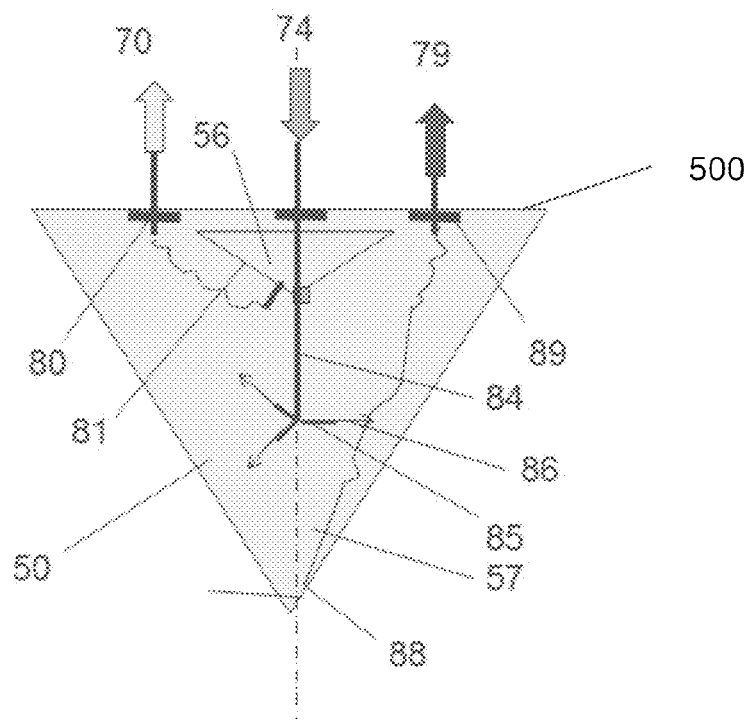
Figure 16:
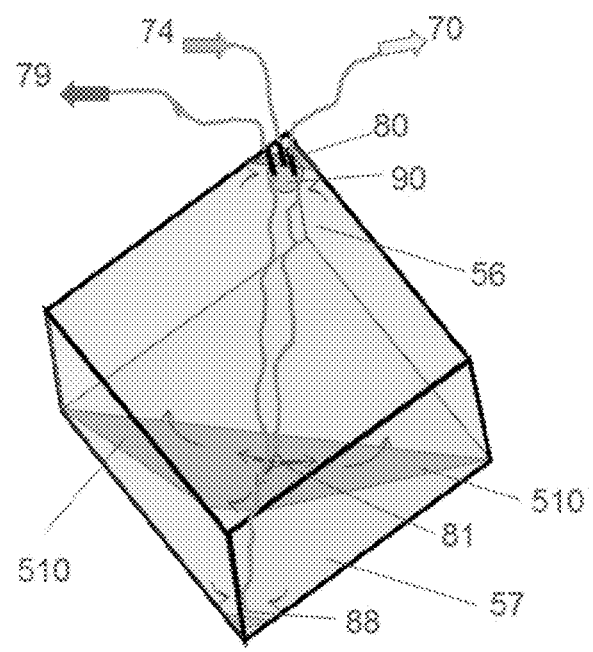
Figure 17:
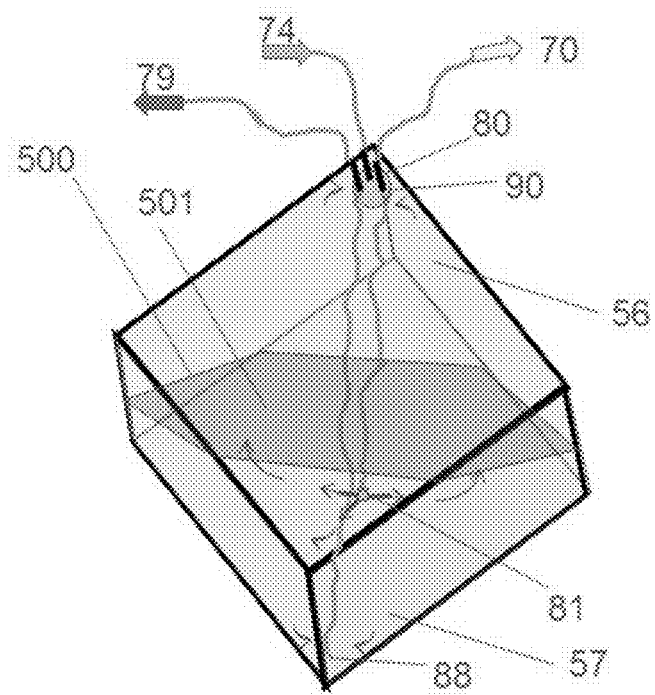

In particular, the polyhedral form of the separator according to the invention is selected from the group consisting of a disphenoid (=a polyhedron bounded by four congruent triangles, as shown in FIGS. 14 and 15), in particular tetrahedron, regular pyramid (=a polyhedron bounded by four congruent triangles and a square, which is not shown), octahedron and cube (shown in FIGS. 16 and 17).

Equally suitable are cones (=composed of the conical shell and a circular blank sheet).

For simple production from a plastic film, disphenoid, in particular tetrahedra, cones and cubes are preferred. The cell separator according to the invention usually has a ratio of height to maximum width in the range from 0.2 to 3, preferably 0.5 to 2, particularly preferably 0.7 to 1.5.

The cell separator according to the invention is preferably connected to a bioreactor or other external systems via ports and connection lines at the top of the separator. This has the advantage that the container can be designed for receiving the separator appliance without a passage, i.e. leak-free. Thereby, without additional safety facilities, the escape of genetically modified production cells may be prevented.

Figure 25:
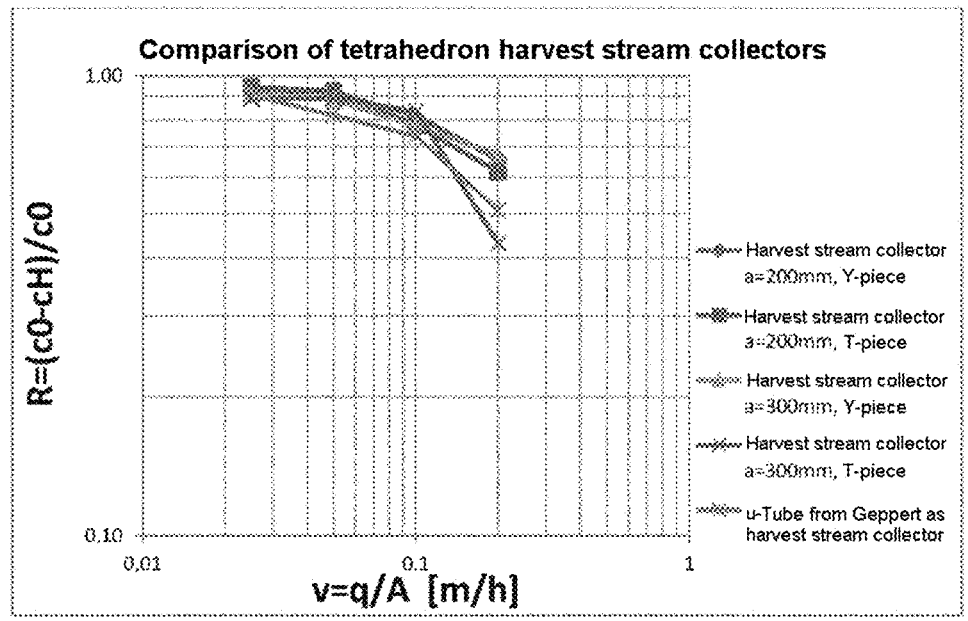

The bioreactor mixture is usually introduced via an internal 84 for introducing the bioreactor mixture along the vertical axis of the plastic bag arranged for operation. Preferably, in the cell separator according to the invention, at the inlet opening of the internal element 84, horizontal distributors 85 are used for uniform horizontal flow distribution of the reactor mixture 74. The feed is distributed in this case by means of annular nozzles or by means of two or more exit openings of horizontally directed internals such as, e.g., T-pieces or downwardly directed internals such as, e.g., Y-pieces over inlet surface 510, preferably in the direction of the corners of inlet surface 510. FIG. 25 shows a comparison between internal 84 for introducing the bioreactor mixture having a single T or Y distributor, and with duplicated T or Y distributors. In the case of the Y distributors, the inlet streams are directed downwards. The effect of the distributor in the case of a small clarifying surface loading v≤0.1 m/h is low. A better retention was achieved using a single T or Y distributor than using duplicated T or Y distributors. At high surface loadings v≥0.1 m/h, the Y distributors having the downwardly directed inlet streams are superior to the T distributors and are correspondingly preferred.

Usually, distributors having from 2 to 8, preferably 2 to 4, horizontally or downwardly directed openings are used, wherein a width c (=distance between two openings) to the edge length D of the plastic bag 0.03≤c/D≤0.25, preferably 0.04≤c/D≤0.15, is usually used. In the case of a conical separator, D is the diameter of the circular blank sheet.

The solids are usually removed from the solids collection region 57 via one or more passages or internals 88 in the vicinity of the lower apex of the separator. The internal 88 is connected to the bioreactor into which the collected cells are returned via the pressure gradient or via pumps. Preferably, the internal 88 is used for the central, vertical removal by suction of the solids (FIGS. 14, 15, 16, 17). This simplifies the production and placing of the separator in the container thereof for operation. In a further preferred embodiment, the takeoff can also be taken off via a passage welded into the apex of the separator. For a leak-free design of the housing, in this case, the flexible connection tube must be laid in the interior of the housing for receiving the separator (i.e. between housing wall and plastic bag).

The harvest stream is usually taken off via an internal 80 which is situated within the plastic bag in the harvest stream collection region 56 above the separation area 500. In a preferred embodiment, a flow inverter 81 for a unified takeoff of the harvest stream 70 separated from the cells (=harvest) from the harvest stream collection region 56 is installed in the harvest stream collection region 56, which is connected to the internal 80 (FIG. 15). This internal 80 usually has the form of an inverted umbrella having the outer contour of the harvest stream collection region 56 (in the case of a tetrahedron, a triangular internal is used), having an edge length or diameter a, wherein 0.25≤a/D≤0.75, preferably 0.4≤a/D≤0.6, particularly preferably can be 0.5.

Usually, the internals 80, 88 and 84 are welded-in passages, to which conduits, preferably flexible tubes for connecting to the bioreactor or other external systems, can be connected.

In a preferred embodiment of the separator according to the invention, in the upper region, on the wall of the plastic bag (tetrahedron) or at a corner (cube), is situated one or more connection plates 90, preferably one, which can also be a cover, which contains the passages for passing through the connection lines, and, in the region of the connection, a support of the separator is made possible. It is usually connected to the housing of the separator during assembly.

The maximum separation area 500 is situated above the inlet surface 510. The separation of the cells proceeds in the vertical separators according to FIGS. 14 to 17 in the conically upwardly expanding container cross section up to the maximum cross section of the separation area 510, according to the positive force difference between gravity and vertical inflow as a result of continuous takeoff of the harvest stream from the harvest stream collection region 56.

The dimensioning of the sedimentation separator depends on the type of cells that are to be retained, the size of the bioreactor and the throughput.

The separation area $A_{erf}$ required results, as in the first embodiment of the invention, from the sedimentation velocity ws, the perfusion rate q/V (media throughput q per unit bioreactor volume V) and the bioreactor volume V according to Eq.1. An efficiency coefficient η takes into account the reduction in performance of technical separators compared with the idealized consideration of an individual particle exposed to flow from below, the falling velocity ws of which, in order to meet the condition for separation, must be a little greater than the inflow velocity=perfusion rate×V/Aerf (Eq.2).

As already discussed:

$$A_{erf} = \frac{Perfusionrate \cdot V}{ws} \quad \text{(Eq. 1)}$$

$$A_{th} = \frac{A_{erf}}{\eta} \quad \text{(Eq. 2)}$$

The theoretical separation area for polyhedral plastic bag separators is determined to an approximation from Eq.5 or Eq.6:

For tetrahedra having the edge length D, for determining the maximum separation area, to a first approximation the following applies:

$$A_{th} = \frac{1}{4}D^2\sqrt{3} \quad \text{(Eq. 5)}$$

Because the takeoff point is structurally somewhat below the maximal cross section given by the edge length of the tetrahedron, the efficiency coefficient η is somewhat less than 1.

The same applies to conical separators, the maximum separation area of which is given by the circular blank sheet diameter D:

$$A_{th} = \frac{\pi}{4}D^2 \quad \text{(Eq. 6)}$$

For cubes having the edge length D, there results as maximum separation area at η=1 a hexagon having the following cross-sectional area:

$$A_{th} = \frac{3}{4}D^2\sqrt{3} \quad \text{(Eq. 7)}$$

During dimensioning of the second embodiment of the separator according to the invention, likewise maintaining laminar flow conditions must be taken into account. During dimensioning of the plastic bag (50), the edge length D and the length LK of the bag that are to be achieved are oriented according to the fill levels to be achieved in the plastic bag. Excessive hydrostatic pressures may possibly be passed on to correspondingly dimensioned, non-product-contact and therefore reusable housings.

Usually, the inlet surface 510 is situated at a height h based on the height of the plastic bag HK of 0.3≤h/HK≤0.7, preferably 0.4 to 0.6. FIG. 26 shows the effect of the height of the inlet surface on the retention in a cube separator.

For the use as intended, the separator is introduced into a container which supports the flexible walls of the plastic bag when the separator is full. Therefore, the shapes of container and separator are preferably matched to one another.

The present invention therefore further relates to a solids separation device comprising a solids separator according to the invention and a container for receiving the solids separator, wherein the container comprises at least:

an interior for receiving the solids separator, wherein the interior is adapted to the shape of the solids separator by means of walls which are adapted to the shape of the solids separator and enclose the interior and delimit it from the exterior, an opening for introducing the solids separator from the top into the container.

Preferably, in particular for the second embodiment of the separation device, the container has a channel via which flexible tubes and/or channels and/or measurement probes can be led up to the cell separation device.

The opening for introducing the cell separation device is preferably closable.

The container according to the invention, in the closed state, is preferably constructed so as to be liquid-tight, that is to say it can be sealed off from the exterior in such a manner that no liquid passes unintentionally from the interior of the container to the exterior.

Figure 24:
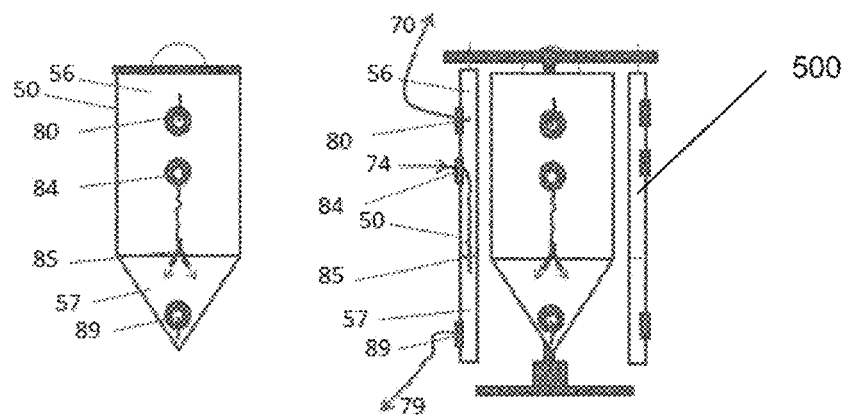

A plastic bag or a plastic bottle is also possible having a rectangular cross section and, in the lower region, a downwardly tapered solids collection region 57 forms for collecting the solids with the aid of gravity (FIG. 24). Internals and passages 80, 88 and 84 can be welded into the plastic bag or plastic bottle. Alternatively, the downwardly tapered solids collection region 57 ends in a neck. Both the plastic bag neck and the plastic bottleneck are then closed with a cover or stopper in which all necessary passages are incorporated. In both embodiments, the shape of the harvest stream collection region 56 can be as desired. These plastic bags or plastic bottles are particularly advantageous for small fermenter volumes of 0.02 to 2l. For operation, one or more plastic bags or plastic bottles are suspended on a stand. For a space-saving application of a plurality of separators in parallel, the suspended plastic bags or plastic bottle of FIG. 24 are advantageous.

The present invention further relates to a bioreactor system consisting of a bioreactor and one of the described cell separation device according to the invention. Preferably, the bioreactor is a single-use reactor, in particular a reactor as described in US 2009-0180933.

The bioreactor system is, for example, a perfusion reactor which can be operated in a known manner. Nutrient medium is continuously fed into the bioreactor and cell culture supernatant low in cells is continuously removed. The perfusion reactor can be operated at high perfusion rates q/V (media throughput q per unit bioreactor volume V), if this is biologically meaningful, and a sufficient separation area is provided. In this case, the flow through the separator is continuous.

Likewise, the perfusion reactor can be operated in such a manner that a culture can initially be grown batchwise. When the medium is consumed to the extent that no significant buildup of biomass is possible any more, via the external cell separator, culture supernatant is taken off which is virtually free of biomass. The space obtained in the bioreactor can then be used to supply fresh nutrient medium, as a result of which further growth and thus higher total biomass productivity are made possible (repeated-batch mode). In this case, the flow through the cell separator is batchwise. This method is suitable, for example, for starter cultures, with which very large bioreactors are to be inoculated, since it can increase the productivity of existing starter culture reactors.

For operating bioreactors, continuous flow through the cell separator according to the invention is preferred.

The bioreactor or perfusion reactor can be used for culturing cells which grow in vitro and in free suspension or on microsupports. Preferred cells include protozoa and also adhesive and non-adhesive eukaryotic cells of human (nerve, blood or tissue cells, and also stem cells of embryonic or adult origin), animal or plant origin, which are capable, e.g., via genetic modification, of producing special pharmaceutical active ingredients such as viruses, proteins, enzymes, antibodies, neurons, tissue cells or diagnostic structures. Particularly preferably, for pharmaceutical high performance production, suitable cells are used, for example ciliates, insect cells, baby hamster kidney (BHK) cells, Chinese hamster ovary (CHO) cells, HKB cells (resulting from the fusion of human HEK 293 cell line with human Burkitt lymphoma cell line 2B8), hybridoma cells and also stem cells.

In an alternative embodiment of the system, one of the described cell separators according to the invention, in batch mode, after termination of the fermentation, before cell removal, is attached to a further bioreactor or a harvest tank with the aim of reducing the cell mass to be applied to the filter and thus of reducing the filter areas required.

The present invention further relates to a method for retaining and recirculating solids, in particular cells, in a flow-bearing vessel, wherein solids-containing medium is supplied continuously or batchwise to the vessel, and solids-free medium is removed from the vessel, characterized in that the vessel is a flow-bearing gamma-sterilizable plastic bag or plastic bottle which, in the lower region, has faces set at an incline, favorably a solids collection region 57 which is tapered at the bottom, in particular conically or pyramidally, for collecting the solids with the aid of gravity. In a particular embodiment of the method, the separation area is formed by inclined channels and preferably a flow velocity prevails which permits the maintenance of laminar flow conditions in accordance with Re<2300, which avoids an efficiency-lowering resuspension of the deposited cells against the earth's gravitational field.

The Reynolds number Re can be calculated according to Eq.7 from the cross section-averaged flow velocity w, the kinematic viscosity v of the flowing medium and the internal diameter d of a channel:

$$Re = (w \cdot d / v) \quad \text{(Eq. 7)}$$

In inclined channels, at the channel inner walls, a lower flow velocity prevails than in the channel centers. The cells sediment in the channels and slide on the lower side of the channels against the direction of flow towards the lower channel ends. The cell culture solution that is freed from the cells is delivered by the channels into a harvest stream collection region 56 which is arranged above the channels, and finally transported out of the vessel.

In a polyhedral or conical separator, d is the width or the diameter of the cross section of the maximum separation area. At the plastic walls, a lower flow velocity prevails than in the channel centers. The cells slide against the direction of flow towards the solids collection region 57. The cell culture solution that is freed from the cells ascends in a harvest stream collection region 56 which is arranged above the separation area and is finally transported out of the vessel.

The method according to the invention can preferably be carried out outside a bioreactor. For this purpose, the cell culture solution containing cells is transported out of the bioreactor into the cell separator according to the invention. Preferably, the cells, before entry into the separator, are cooled in an external vessel, in order to slow metabolism and thus counteract a productivity-decreasing undersupply of the cells. In a cooled suspension, an oxygen supply to the sedimented cells is not necessary. In most cases, cooling the cell culture solution to the ambient temperature of the separators is completely sufficient, and so, in addition to the desired metabolic effect, convection flows are safely avoided. For monitoring the adequate supply of the cells, the separator can be equipped with at least one single-use sensor, e.g. for measuring the oxygen concentration and/or the pH. Accommodation of the sensors is possible not only in the walls, but also in the connection line to the bioreactor or the harvest vessels.

The method according to the invention permits effective retention and recirculation of cells in a continuous-flow sterile plastic bag. During the retention and recirculation, only moderate shear forces act on the cells which for the most part are tolerated well by the cells. The cells in the separation device are kept at fermentation temperature or a lowered temperature level and supply with nutrients is provided.

Hereinafter, exemplary embodiments of the invention are described in more detail with reference to drawings without restricting the invention thereto.

FIG. 1 Schematic depiction of the single-use solids separators according to the invention with lamellae pack.

Figure 2:
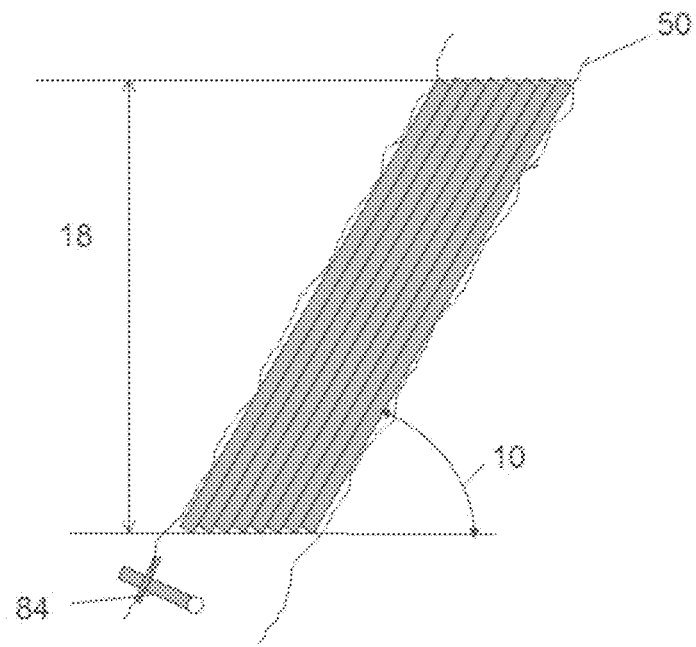

FIG. 2 Schematic depiction of a lamellae pack 1 (longitudinal section)

Figure 3:
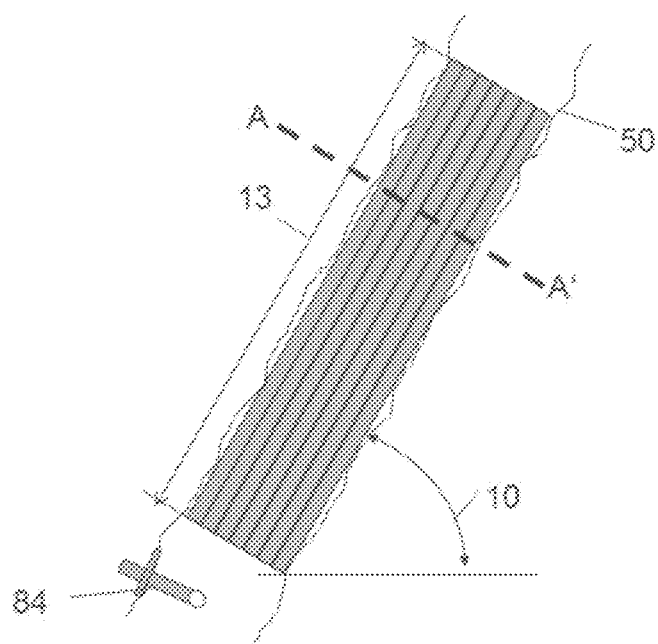

FIG. 3 Schematic depiction of a lamellae pack 1 (longitudinal section)

FIG. 4 Diagram of the structure of various lamellae packs (cross section AA' of FIG. 3)

Figure 5:
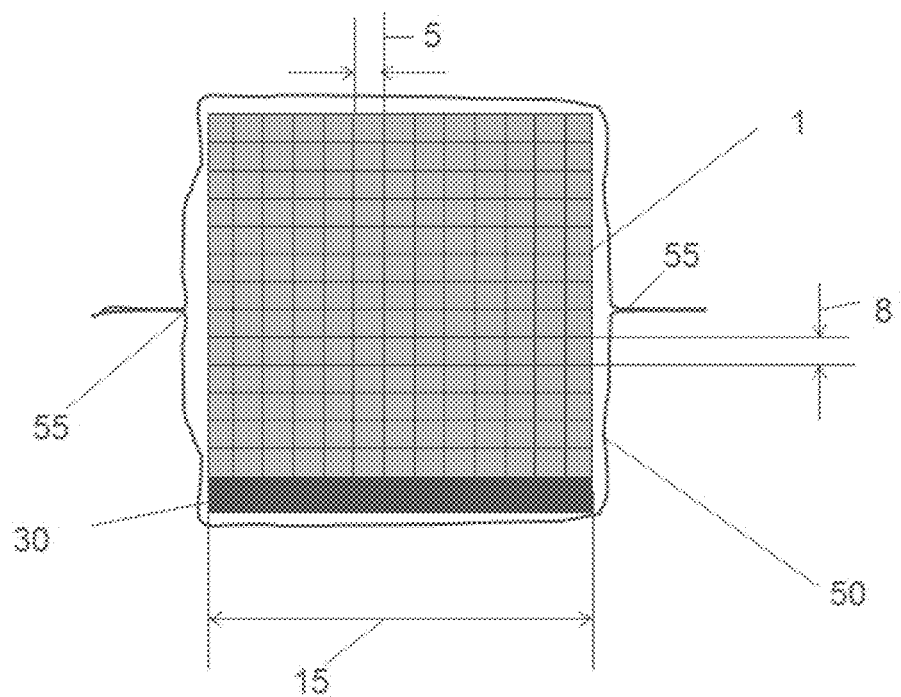

FIG. 5 Diagram of the application of the plastic bag 50 on a lamellae pack 1 (cross section AA' of FIG. 3)

Figure 6:
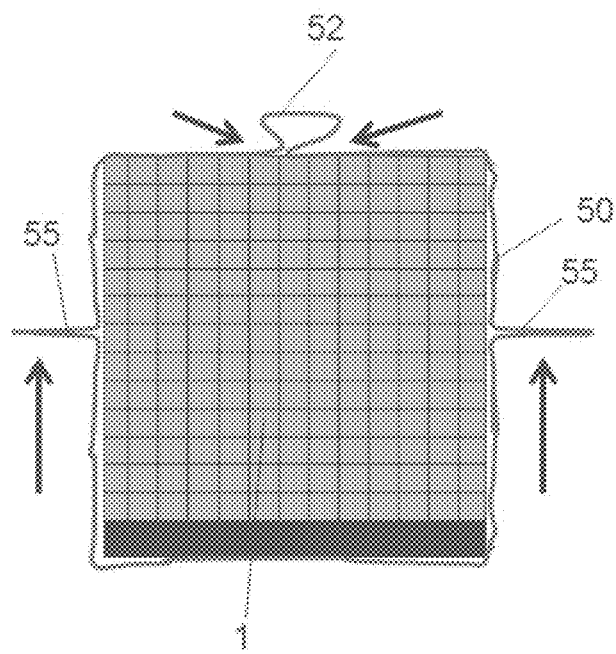
Figure 7:
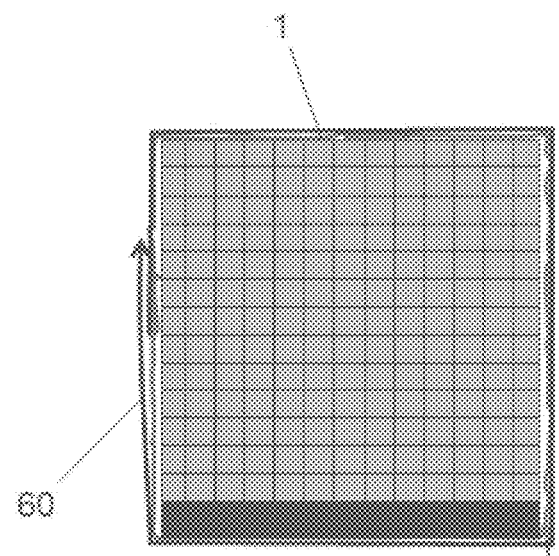

FIG. 6 and FIG. 7 Stretching and fastening of the plastic bag 50 on a lamellae pack 1 (cross section)

Figure 8:
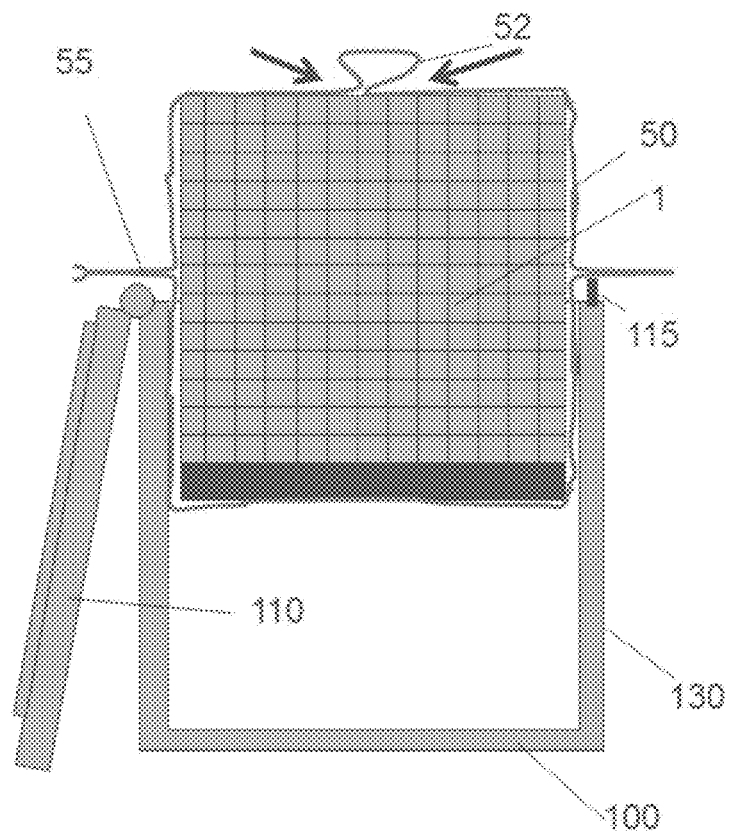
Figure 9:
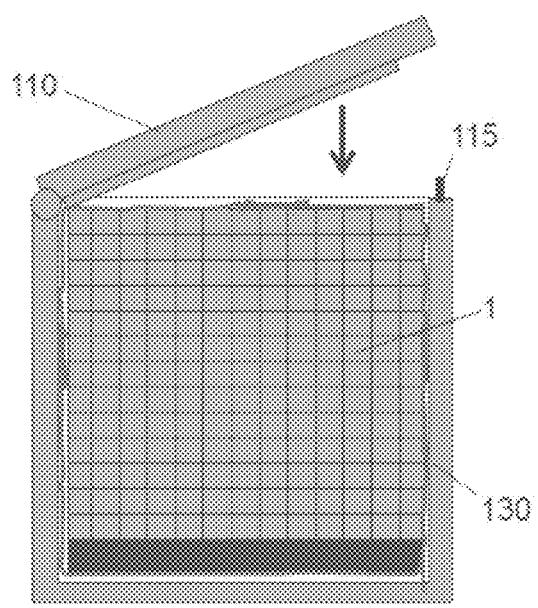

FIG. 8 and FIG. 9 Alternative stretching and fastening of the plastic bag 50 on a lamellae pack 1 with the aid of frame 130 and cover 110 (cross section)

Figure 10:
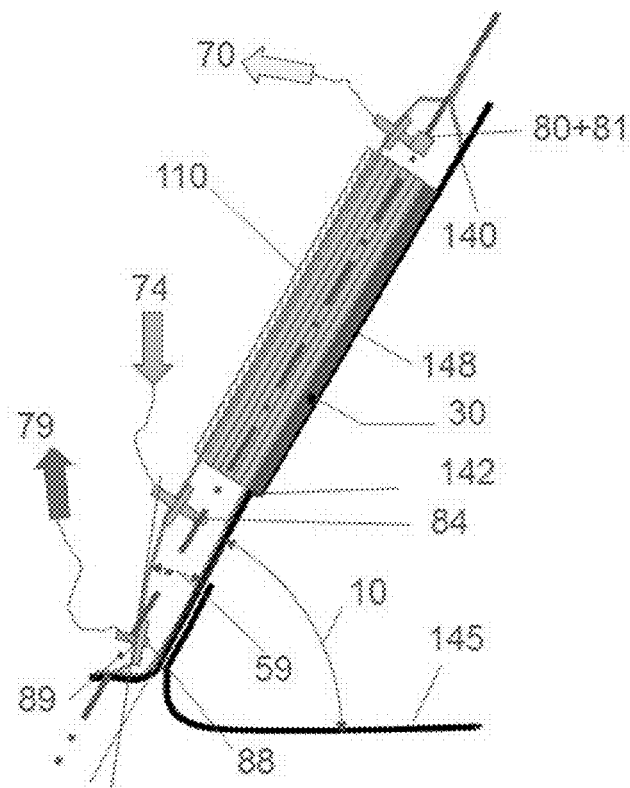

FIG. 10 Side views of the solids separators according to the invention with lamellae pack 1 on stand 140.

FIG. 11 Front views of the solids separators according to the invention with lamellae pack 1 on stand 140.

FIG. 12 Longitudinal sections of the solids separators according to the invention with lamellae pack 1 on stand 140 with frame 130 and cover 110.

FIG. 13 Front views of the solids separators according to the invention with lamellae pack 1 on stand 140 thereof with frame 130 and cover 110.

FIG. 14 Schematic three-dimensional depiction of the solids separators according to the invention in the disphenoidal embodiment FIG. 15 Schematic longitudinal section of the solids separators according to the invention in the disphenoidal embodiment with flow inverter 81

FIGS. 16 and 17 Schematic depiction of the solids separators according to the invention in the cubic embodiment.

FIG. 18 Process diagram of a perfusion reactor. In order to reduce the respiratory activity of the cells in the bioreactor sequence, the temperature thereof is decreased to a lower level in a cooling device as soon as possible after the takeoff. In this manner, the cells in the cell separator are prevented from having too long a residence in an oxygen-limited state, which could damage the cells physiologically. In the example shown, the separator 640 consists of a separation bag 620 and an integrated cooling device 600. The liquid streams between bioreactor 610 and separator 640 are established via the low-shear pumps 630 and 631. Other circuitry, e.g. the positioning of one of the two pumps 630 and 631 in the bioreactor sequence, are likewise conceivable.

Figure 19:
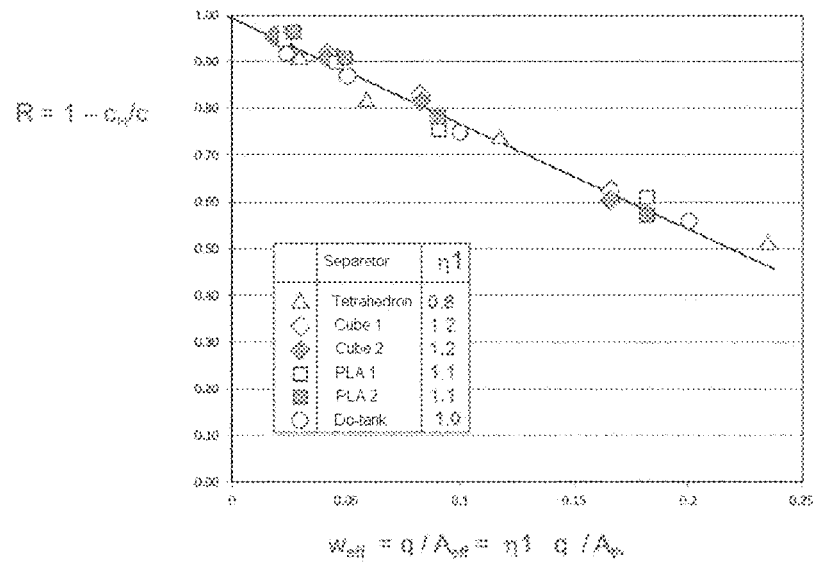

FIG. 19 Comparison of the separation systems

Figure 20:
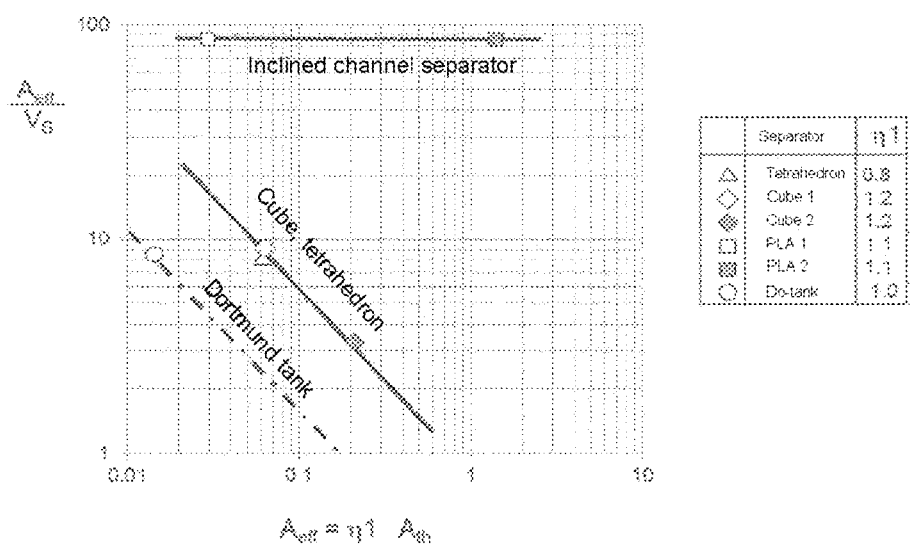

FIG. 20 Comparison of the separator volumes per unit separation area.

Figure 21:
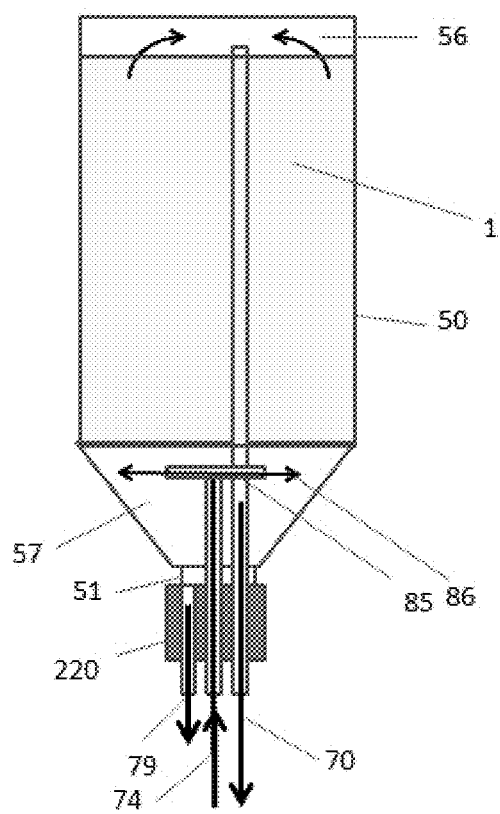

FIG. 21 Longitudinal sections of the bottle separator with trays as separation area 1, horizontal flow distributor 85 and stopper 220.

Figure 22:
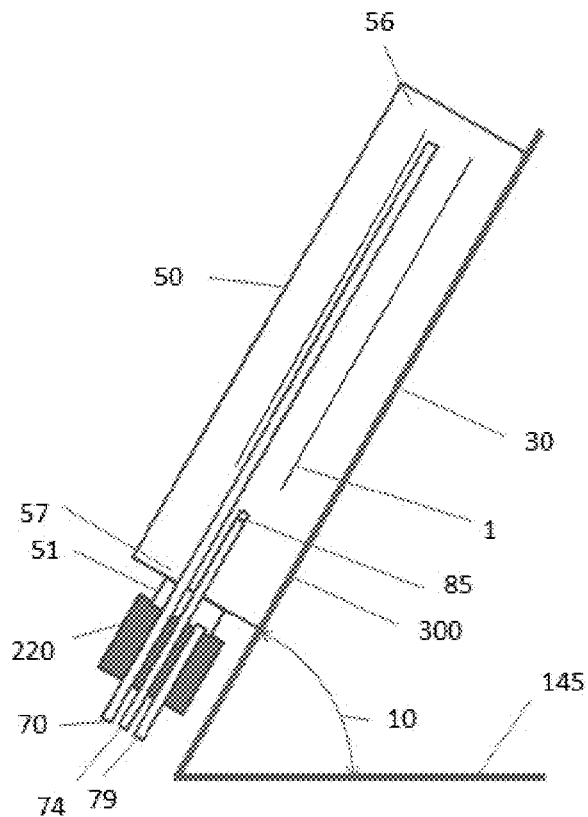

FIG. 22 Lateral section of the bottle separator according to FIG. 21 on its stand.

Figure 23:
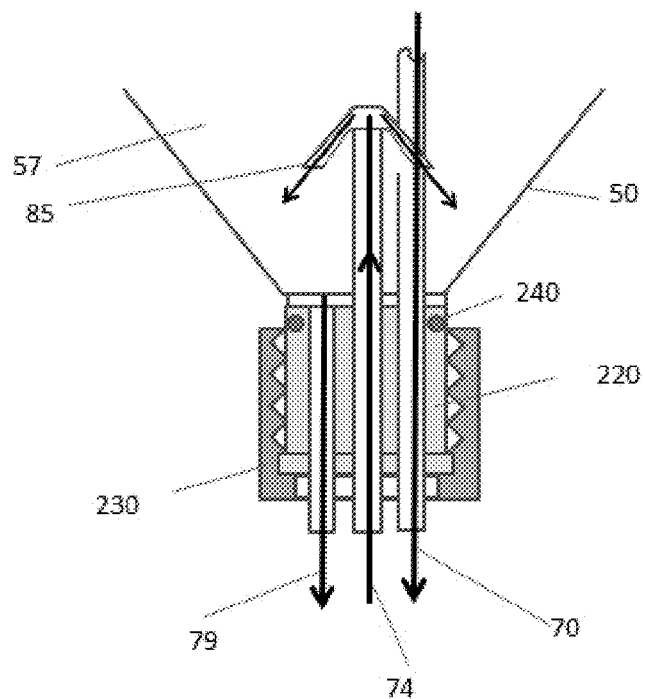

FIG. 23 Details of a stopper 220 with collar 230 and flow distributor 85 with downwardly directed inlet flows FIG. 24 Front views of a suspended plastic bag (=Bag-Settler) as solids separator and lateral section on stand.

FIG. 25 shows the effect of various flow distributors 85 on the retention performance R under a varying effective ascension velocity v=q/Aeff.

REFERENCE SIGNS

1 Lamellae pack/separator area
5 Ridge width
8 Plate separation
10 Angle
13 Length
15 Width
18 Height
30 Support plate
50 Plastic bag or plastic bottle
51 Neck
52 Excess/fold
55 Weld seam
56 Harvest stream collection region
57 Solids collection region
58 Angle
59 Angle
60 Fastening strip
70 Harvest stream (harvest)
74 Bioreactor mixture/feed
79 Recirculation
80 Passage
81 Flow inverter
84 Passage
85 Flow distributor in particular horizontal distributor or flow distributor having downwardly directed inlet flows
86 Inlet flow
88 Central removal by suction
89 Passage
90 Connection plate
100 Housing
110 Cover
112 Elongation
115 Fastening element
130 Frame
140 Stand
142 Projection
145 Stand foot
148 Support
200 Vibrator
210 Assembly plate
220 Cover or stopper
230 Collar nut
240 O ring
Profiles of a Lamellae Pack
311 Lamellae pack
320 Rectangular profile
321 Lamellae pack
330 Round profile
331 Lamellae pack
340 Round profile
341 Lamellae pack
350 Hexagonal profile
351 Lamellae pack
500 Theoretical maximum separator area
501 Separator region
510 Inlet surface
600 Cooling device
610 Bioreactor
620 Separation device
630, 631 Pumps
640 Separator=Separation bag+cooling device optionally integrated in the stand or container
650 Culture medium Hereinafter, studies are described on the applicability of the devices according to the invention without restricting it thereto.

Particle System

For the simulation of cells, the particle system polyacrylonitrile X polymer "PAN-X" is used. The water-insoluble polymer is principally used in the clothing industry for producing fibers. Hereinafter is an extract from the product data sheet of the manufacturer Dralon GmbH, Dormagen.

| Name | PAN-X |
| --- | --- |
| Chemical formula | $[C_3H_3N]_n$ |
| Administration form | Powder |
| Particle form | spherical |
| Color | white |
| Density | 1.18 g/m$^3$ |
| Particle size distribution | 97 vol % ≤ 50 μm |
| Solubility in water | insoluble |
| Ignition temperature | 485° C. |

The particle size distribution shows the most frequent particle diameter between 15 and 30 μm measured using the Mastersizer laser diffraction measuring instrument from Malvern, which corresponds roughly to eukaryotic cells (CHO, BHK).

Separation Systems

Inclined Channel Separator

For purposes of comparison, a study was made of a large and a small plate separator made of stainless steel according to WO03/020919 having theoretical separation areas of $A_{th}$=1.42 m$^2$ and $A_{th}$=0.027 m$^2$ as a model of the separator according to the invention according to FIG. 2. The large separator has 20 plates which are accommodated in a separator volume of 17.4 l. The small lamellae separator consists of 4 plates in a separator volume of 0.3 l.

Cube Separator

Two cubes were produced as a hydrodynamic model having the edge lengths D=200 mm and D=400 mm from Plexiglass plates. The upper corner of the cube had an opening for the passage of flexible tubes. One internal for flow distribution (also termed (flow) distributor 85) of the particle suspension in the form of a T-piece or Y-piece (in each case two inlets) fastened to a flexible tube was inserted up to the center (h=50% HK) of the plastic model. The width of the distributors c was varied. Via a further flexible tube extending to the lower cone apex (solids collection region 57 also collector), the sediment was taken off vertically upwards in a flow-inverting manner. Via a further passage, a plastic tube was fastened for collecting the clear phase=passage 80, in such a manner that the clear phase (=harvest stream 70) was taken off from the surface directed downwards (U-tube) in a flow-inverting manner. The gradual cross section expansions towards the lower and upper separator apex permit a good flow harmonization and already function thereby as flow collectors (solids collection region 57 at the bottom, harvest stream collection region 56 at the top), which should also function sufficiently well without flow-inverting internals.

Tetrahedral Separators

The tetrahedron was produced as a Plexiglass model from equilateral triangles having an edge length D=400 mm Opposite the corner, which was selected as conical solids collection region 57, the solids separator was open at the top. Via the openings, various passages for introduction and takeoff of suspension (=feed 74), sediment and clear run (=harvest stream 70) could be installed. At the passages, generally flexible tubes, distributor and plastic tube for collecting the clear phase (=passage 80) were constructed and positioned in an analogous manner to the cube.

The tetrahedron differs in its flow characteristics compared with the cube primarily in that a flow-favoring tapering is only present downwards to the return collector and the clear phase is collected at the point of the largest surface area. For uniform takeoff, in the tetrahedron, therefore, a flow distributor 85 placed in this maximum separation area is used.

The separation area $A_{th}$ in the unit studied was 0.069 m² at a volume of 7.6 l.

Vertical Separator with Conical Feed—Dortmund Tank Type

This vertical separator is frequently used in the wastewater industry. The separator studied consisted of a cylindrical shell having a cross section of 145 mm which forms a collection funnel in the lower region and, in the upper region, has a centrally placed conical feed having a cross section of 51 mm. Both elements were fabricated from glass. The non-clarified liquid was introduced via the conical feed from the top into the cylindrical region (vertical separation region) and ascended into the separation region, whereas the suspended matter sedimented in the collection funnel. At the top end of the separation region, the clear phase was collected at four points. The vertical separator studied had a volume of 1.7 l of a separator area $A_{th}$ of 0.014 m².

Methods

Analytical Method

The sample is filtered off using a Buchner funnel (pore size<2 μm), the filter paper is dried at 140° C. and weighed. A drying balance (Sartorius MA45) was used therefor.

Experimental Procedure

PAN-X 3 g/l was provided in the reservoir tank and introduced into the respective separator by means of peristaltic pumps (Watson-Marlow Du323). The desired ascension velocity v (v=q/Ath, wherein q is the harvest stream with which the separator is loaded for a given perfusion rate and bioreactor volume V) is set via the pump rate of the peristaltic pumps q.

The particle suspension is first pumped in circulation. After a waiting time of two hydrodynamic residence times, for establishing stationary conditions, the sampling from the harvest stream was started.

The sample volume is oriented according to the particle mass on the filter. This should be approximately 100 mg±25 mg within the limits of measurement accuracy. Sample volumes result therefrom of 40 to 800 ml for determining the particle concentration, which were measured in triplicate.

Results

TABLE 1

| Separator | Geometry | | | R = 1 − $c_H$/c 1 | w = q/Ath m/h | w_eff = w/ηDo m/h |
|---|---|---|---|---|---|---|
| Tetrahedron | A | m² | 0.0692 | 0.91 | 0.03 | 0.0294 |
|  | d | mm | 400 | 0.82 | 0.05 | 0.0588 |
|  | VS | L | 6.42 | 0.74 | 0.10 | 0.1176 |
|  | ηDo | — | 0.8 | 0.51 | 0.20 | 0.2353 |
| Cube 1 | A | m² | 0.052 | 0.96 | 0.03 | 0.0208 |
|  | d | mm | 200 | 0.92 | 0.05 | 0.0417 |
|  | VS | L | 8.00 | 0.83 | 0.10 | 0.0833 |
|  | ηDo | — | 1.2 | 0.63 | 0.20 | 0.1667 |
| Cube 2 | A | m² | 0.208 | 0.95 | 0.03 | 0.0208 |
|  | d | mm | 400 | 0.91 | 0.05 | 0.0417 |
|  | VS | L | 64 | 0.81 | 0.10 | 0.0833 |
|  | ηDo | — | 1.2 | 0.61 | 0.20 | 0.1667 |
| PLA 1 | A | m² | 0.0274 | 0.95 | 0.03 | 0.0227 |
|  | Z | 1 | 4 | 0.90 | 0.05 | 0.0455 |
|  | VS | L | 0.375 | 0.76 | 0.10 | 0.0909 |
|  | ηDo | — | 1.1 | 0.61 | 0.20 | 0.1818 |
| PLA 2 | A | m² | 1.42 | 0.96 | 0.03 | 0.0227 |
|  | Z | — | 21 | 0.92 | 0.05 | 0.0455 |
|  | VS | L | 18 | 0.79 | 0.10 | 0.0909 |
|  | ηDo | — | 1.1 | 0.59 | 0.20 | 0.1818 |
| Dortmund tank | A | m² | 0.0142 | 0.93 | 0.03 | 0.9286 |
|  | d | mm | 145 | 0.87 | 0.05 | 0.8704 |
|  | VS | L | 1.7 | 0.75 | 0.10 | 0.7506 |
|  | ηDo | — | 1 | 0.56 | 0.20 | 0.5617 |

Comparison of the separation systems shows the expected fall in the degree of retention R with increasing media stream or harvest stream q or the effective ascension velocity $v=q/A_{eff}$ (FIG. 19). The effective ascension velocity results by introducing the efficiency coefficient η1, which identifies the differing retention performance of the maximum area used of the separators compared with the Dortmund tank. FIG. 19 indicates that the separators, after addition of this efficiency coefficient, can be described by a joint line of best fit.

The performance of the separators is compared in FIG. 20. This presentation shows how many separator volumes are necessary in order to accommodate the effective separation area Small separator volumes are desirable in cell cultures in order to minimize residence times outside the fermentation space supplied. In this comparison, the inclined channel separators come out favorably, which can be operated, independently of the scale, with very high separation areas per unit separator volume greater than 50 l/m. This example makes clear the outstanding scalability of these separator systems. In contrast thereto, in the case of the vertical separators, considerably greater volume is required in order to develop therein the horizontal separation area. In addition, the efficiency of accommodation in the scale enlargement falls with V=A$^{3/2}$. Surprisingly, the efficiency of the single-use models, the cubes and the tetrahedron is considerably superior to the standard system of the Dortmund tank, and so these very simple and inexpensive systems can be used in considerably larger bioreactors (up to approximately 6-times) than the Dortmund tank. A further adaptation (geometry and/or position) of the feed distributors and harvest stream collectors could lead to an optimization of the degree of retention R.

The work which led to this application was funded in accordance with the financial aid agreement "Bio.NRW: MoBiDik—Modular bioproduction—disposable and continuous" (funding code w1004ht022a) under the European regional development fund (ERDF).

The invention claimed is:

1. A solids separator for retaining and recirculating solids from a reactor mixture, comprising a flow-bearing sterilizable plastic bag or plastic bottle and, within the plastic bag or plastic bottle:
   in the upper region, one or more passages/internals for withdrawing from a harvest stream collection region a harvest stream that is separated from the solids,
   in the upper segment of a central region, a separation region having a separation area, which, during operation, is inclined at an angle of 0° to 80° to the horizontal,
   in the lower segment of the central region, one or more passages or internals for a uniform horizontal flow distribution of the reactor mixture over an introduction surface, wherein the separation area is situated above the introduction surface,
   in the lower region a solids collection region that is tapered at the bottom for collecting the solids using gravity.

2. The solids separator of claim 1, wherein solids collection region has one or more passage or internals for withdrawing the solids.

3. The solids separator of claim 2, wherein the plastic bag or plastic bottle has a rectangular cross section, wherein the downwardly tapered solids collection region ends in a neck which is closed with a cover or stopper, wherein the cover or stopper has all passages.

4. The solids separator of claim 1, wherein the solids collection region is tapered downwards conically or pyramidally.

5. The solids separator of claim 1, which comprises at least one single-use sensor in the interior.

6. The solids separator of claim 1, wherein the separation region consists of a multiplicity of adjacently arranged channels in a lamellae pack and the separation area during operation is inclined at an angle to the horizontal of 30° to 80°.

7. The solids separator of claim 6, wherein the lamellae pack consists of a plurality of ridgeplates stacked one above the other which form the channels of the lamellae pack.

8. The solids separator of claim 7, wherein the ratio of ridge height to channel width hs/d is $0.01 \leq hs/d \leq 5$ with the restriction.

9. The solids separator of claim 6, wherein the channels have a channel length L of 30% to 95% of a length LK of the plastic bag or plastic bottle.

10. The solids separator of claim 1, wherein the plastic bag is polyhedral or conical and wherein the plastic bag, during operation, is placed such that the solids collection region which is tapered at the bottom is formed by the walls of the plastic bag and the apex or corner of the polyhedron or of the cone.

11. The solids separator of claim 10, wherein the plastic bag is a disphenoid, a regular pyramid, an octahedron or a cube.

12. The solids separator of claim 1, comprising a container for receiving the plastic bag, wherein the container comprises at least:
   (a) an interior for receiving the plastic bag, wherein the interior is adapted to the shape of the plastic bag by means of walls which are adapted to the shape of the plastic bag and enclose the interior and delimit it from the exterior, and (b) an opening for introducing the plastic bag from the top into the container.

13. The solids separator of claim 1, wherein the separation area does not comprise plates.

14. A bioreactor system comprising a bioreactor connected to a solids separator as claimed in claim 1.

15. A method for retaining and recirculating solids in a flow-bearing vessel of the solids separator of claim 1, comprising
   supplying solids-containing medium continuously or batchwise to the vessel, and
   removing solids-free medium from the vessel,
      wherein the vessel is the flow-bearing sterilizable plastic bag or plastic bottle which, in the lower region, comprises faces set at an incline, favorably the solids collection region, which is tapered conically at the bottom for collecting the solids with the aid of gravity,
   wherein the solids comprise cells.

* * * * *